(12) United States Patent
Vidal et al.

(10) Patent No.: US 10,729,641 B2
(45) Date of Patent: *Aug. 4, 2020

(54) ORDERED MACROPOROUS MATERIALS

(71) Applicants: L'OREAL, Paris (FR); REGENTS OF THE UNIVERSITY OF MINNESOTA, Minneapolis, MN (US)

(72) Inventors: Laurent Vidal, Paris (FR); Andreas Stein, Saint Paul, MN (US); David Josephson, St. Louis Park, MN (US)

(73) Assignees: REGENTS OF THE UNIVERSITY OF MINNESOTA, Minneapolis, MN (US); L'OREAL, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 14/738,346

(22) Filed: Jun. 12, 2015

(65) Prior Publication Data
US 2016/0361248 A1  Dec. 15, 2016

(51) Int. Cl.
| | | |
|---|---|---|
| *A61K 8/891* | (2006.01) | |
| *A61K 8/25* | (2006.01) | |
| *A61K 8/81* | (2006.01) | |
| *A61K 8/02* | (2006.01) | |
| *A61K 8/19* | (2006.01) | |
| *A61Q 1/02* | (2006.01) | |
| *C01G 49/02* | (2006.01) | |
| *C01G 23/047* | (2006.01) | |
| *C09C 1/40* | (2006.01) | |
| *C09C 3/12* | (2006.01) | |
| *C09C 1/36* | (2006.01) | |
| *C09C 1/24* | (2006.01) | |
| *C09C 1/04* | (2006.01) | |
| *C09C 1/02* | (2006.01) | |
| *C09C 1/30* | (2006.01) | |

(52) U.S. Cl.
CPC ............ *A61K 8/891* (2013.01); *A61K 8/0279* (2013.01); *A61K 8/19* (2013.01); *A61K 8/25* (2013.01); *A61K 8/8152* (2013.01); *A61Q 1/02* (2013.01); *C01G 23/047* (2013.01); *C01G 49/02* (2013.01); *C09C 1/02* (2013.01); *C09C 1/043* (2013.01); *C09C 1/24* (2013.01); *C09C 1/3081* (2013.01); *C09C 1/3684* (2013.01); *C09C 1/407* (2013.01); *C09C 3/12* (2013.01); *A61K 2800/26* (2013.01); *A61K 2800/412* (2013.01); *A61K 2800/436* (2013.01); *A61K 2800/624* (2013.01); *A61K 2800/651* (2013.01); *C01P 2004/03* (2013.01); *C01P 2006/16* (2013.01); *C01P 2006/17* (2013.01)

(58) Field of Classification Search
None
See application file for complete search history.

(56) References Cited

U.S. PATENT DOCUMENTS

| | | | |
|---|---|---|---|
| 2,676,182 A | 4/1954 | Hebert et al. | |
| 3,627,851 A | 12/1971 | Brady | |
| 3,772,247 A | 11/1973 | Flannigan et al. | |
| 4,132,560 A | 1/1979 | Marquisee et al. | |
| 4,935,484 A | 6/1990 | Wolfgruber et al. | |
| 5,082,706 A | 1/1992 | Tangney | |
| 5,248,739 A | 9/1993 | Schmidt et al. | |
| 5,302,685 A | 4/1994 | Tsumura et al. | |
| 5,319,040 A | 6/1994 | Wengrovius et al. | |
| 6,403,065 B1 | 6/2002 | Chevalier et al. | |
| 6,680,013 B1 | 1/2004 | Stein et al. | |
| 6,863,847 B2 * | 3/2005 | Fu | B82Y 20/00 264/1.21 |
| 2003/0116062 A1 | 6/2003 | Anselmann et al. | |
| 2005/0019285 A1 | 1/2005 | Lee et al. | |
| 2005/0036964 A1 | 2/2005 | Camus et al. | |
| 2006/0002875 A1 * | 1/2006 | Winkler | A61K 8/25 424/63 |
| 2009/0133605 A1 | 5/2009 | Butler et al. | |
| 2009/0304756 A1 | 12/2009 | Dahne et al. | |
| 2012/0244202 A1 * | 9/2012 | Simonnet | A61K 8/8152 424/401 |

FOREIGN PATENT DOCUMENTS

| | | |
|---|---|---|
| EP | 0 242 219 A2 | 10/1987 |
| EP | 0 285 886 A1 | 10/1988 |
| EP | 0 765 656 A1 | 4/1997 |

(Continued)

OTHER PUBLICATIONS

Josephson (Josephson, Three-Dimensionally Ordered Macroporous Materials for Use as Color Pigments, Ultraviolet Reflectors, and Modified Thermal Emission Devices, Doctoral dissertation, listed on the Mar. 28, 2017 IDS, "Jan. 2014" on cover, "© David Peter Josephson 2013" on p. 2).*

(Continued)

*Primary Examiner* — H. Sarah Park
(74) *Attorney, Agent, or Firm* — Viksnins Harris Padys Malen LLP (57) ABSTRACT

The present invention relates to an inorganic material comprising particles of three-dimensional ordered macroporous structure comprising spherical pores, said pores having an average pore diameter ranging from 50 nm to 10 μm, the pore diameter varying by no greater than 20%, the surface of said pores being coated by an absorber agent of the visible wavelength spectrum, said particles having an average largest dimension ranging from 1 to 50 μm, and wherein said particles are coated with at least a hydrophobic component.

The invention further relates to a process for preparing said inorganic material.

17 Claims, 3 Drawing Sheets

(56) References Cited

FOREIGN PATENT DOCUMENTS

| | | |
|---|---|---|
| FR | 2 778 561 A1 | 11/1999 |
| FR | 2 810 881 A1 | 1/2002 |
| FR | 2 848 821 A1 | 6/2004 |
| FR | 2 848 822 A1 | 6/2004 |
| FR | 2 872 032 A1 | 12/2005 |
| FR | 2 873 021 A1 | 1/2006 |
| JP | S61-194009 A | 8/1986 |
| WO | 01/43714 A1 | 6/2001 |
| WO | 01/88044 A1 | 11/2001 |
| WO | 2007/031345 A2 | 3/2007 |
| WO | 2008/141971 A2 | 11/2008 |
| WO | WO 2008141971 A2 * 11/2008 ............... A61K 8/19 |

OTHER PUBLICATIONS

Aguirre et al., "Tunable Colors in Opals and Inverse Opal Photonic Crystals", Materials Views, Advanced Functional Materials, 2010, pp. 2565-2578.

Blanford et al., "Tuning Solvent-Dependent Color Changes of Theree-Dimensionally Ordered Macroporous (3DOM) Materials Through Compositional and Geometric Modifications" Advanced Materials, 2001, vol. 13, 1, pp. 26-29.

"Encyclopedia of Polymer Science and Engineering", vol. 15, (1989), pp. 264-271.

Schroden, Rick C., et al., "Optical Properties of Inverse Opal Photonic Crystals", Chem. Mater. vol. 14, No. 8, (2002), pp. 3305-3315.

Zou, D., et al., "Model Filled Polymers. V. Synthesis of Crosslinked Monodisperse Polymethacrylate Beads", Journal of Polymer Science: Part A: Polymer Chemistry, vol. 30, (1992), pp. 137-144.

Josephson, David Peter, "Three-dimensionally ordered macroporous materials for use as color pigments, ultraviolet reflectors, and modified thermal emission devices," Doctoral Dissertation retrieved from the University of Minnesota Digital Conservancy, <http://hdl.handle.net/11299/171236>, published Apr. 13, 2015.

Aug. 10, 2016 International Search Report issued in International Application No. PCT/EP2016/063189.

Aug. 10, 2016 Written Opinion issued in International Application No. PCT/EP2016/063189.

* cited by examiner

ORDERED MACROPOROUS MATERIALS

GOVERNMENT RIGHTS

This invention was made with government support under DE-FG02-06ER46348 awarded by the Department of Energy. The government has certain rights in the invention.

PARTIES TO A JOINT RESEARCH AGREEMENT

This application is a result of activities undertaken within the scope of a joint research agreement between l'Oreal, through its affiliate L'OREAL US Products Inc., and the Regents of the University of Minnesota that was in effect on or before the date the research leading to this application was made. CL TECHNICAL FIELD The present invention relates to novel ordered macroporous materials, and cosmetic composition containing such materials useful for optically enlightenment or for modifying the color of human keratinous material and for homogenizing the color of complexion by an immediate effect.

BACKGROUND ART

Ordered Macroporous inorganic structures providing particular reflectance properties are known. They are generally known as inverse opals.

The manufacture of such ordered macroporous inorganic structures is also well known in the art.

Document U.S. Pat. No. 6,680,013 in particular provides a method of forming an inorganic macroporous material by forming a colloidal crystal template of a sample of organic polymer particles, the colloidal crystal template comprising a plurality of organic polymer particles and interstitial spaces there between; adding an inorganic precursor composition comprising a noncolloidal inorganic precursor to the colloidal crystal template such that the precursor composition permeates the interstitial spaces between the organic polymer particles; converting the noncolloidal inorganic precursor to a hardened inorganic framework; and removing the colloidal crystal template from the hardened inorganic framework to form such macroporous material.

Inverse crystal compounds or inverse opals are also known from WO2008/141971 and US2006/0002875.

However, implementing such three-dimensional ordered macroporous inorganic structures within cosmetic compositions has been attempted but has not been found satisfactory until now in particular as far as loss in the dyeing efficacy has been stated.

Indeed, when cosmetic compositions containing said inverted opals are deposited onto supports, specifically keratinic material, it has been observed that the color intensity and saturation decrease dramatically to provide brownish or greyish shades.

There is therefore a need of inverted opals containing cosmetic compositions which afford color intensity when deposited onto keratinic substrates without dye nor colored pigment.

It is frequent that people with colored skin wish to lighten it and in general use biologically active lightening agents such as hydroquinone and its derivatives, kojic acid and its derivatives, azelaic acid, arbutin and its derivatives or alpha-hydroxyacids.

Some people also use these bleaching agents to mitigate, or even eliminate, skin dyschromias occurring either with age or following exposure to UV radiation, with the mask of pregnancy, or with any other skin pathology.

Such bleaching agents act by modifying the biological activity of melanocytes and thereby limit the pigmentation due to the formation of melanin.

As a result, the effects of such bleaching agents appear only slowly, meaning several days, after the iteratively and prolonged use.

On the other hand, these bleaching agents do not modulate the color of enlightened skin as far as they act only on the endogenous biosynthesis of melanin. Furthermore, some of these agents such as hydroquinone or its derivatives are to some extent cytotoxic. More broadly, these bleaching agents sometimes induce allergic phenomena or severe skin irritation.

Therefore, several proposals have been made to afford cosmetic compositions trying to give an immediate enlightenment of the skin complexion.

It is common for people wishing to enlighten the color of their skin or alleviate dyschromias with an immediate perception, to use cosmetic compositions giving enlightenment of the skin complexion but with a whitish appearance. These compositions contain white diffusing pigments ensuring their opacity and covering power, necessary to achieve the desired effect. Moreover, they create an effect of particularly undesirable visible greyish color on the dark skin colors, notably of black color. In order to limit this undesirable greyish effect, the publication FR 2 872 032 proposes cosmetic compositions containing solid particles of refractive index included between 1.2 and 1.5, stemming from the family of organopolysiloxane elastomers, a liquid binder with a refractive index between 1.2 and 1.6, and a coloring agent so that the h index value is included between 40 and 70° and the saturation C value between 20 and 50. Although the skin color obtained after application of compositions containing these ingredients is less mat than with those described in the publications FR 2 848 821 (US2005/036964) and FR 2 848 822 (US2005/019285) as discussed herein after, the effect of enlightenment remains unfortunately slightly perceivable with no possible complexion modulation. Moreover, the covering power creates opacity which makes lose natural appearance of skin, its transparency and clarity. In particular, it generates a gray and muddy complexion effect.

The publications FR 2 778 561 (U.S. Pat. No. 6,403,065), FR 2 810 881, FR 2 873 021 and WO2001/43714 propose the use of optical brightening agents or more generally fluorescent agents, eventually in combination with skin bleaching agents, UV filters, anti-aging products or moisturizing agents. However, the effect of skin enlightenment is not completely satisfactory and does not allow a color modulation that fit as much as desirable the color shade of the various complexions.

To address the above concerns, the publications FR 2 848 821 and FR 2 848 822 propose cosmetic compositions containing at least one dye and at least a reflective particles the color of which goes from pinkish beige to orange-beige, characterized by a color h value between 50° and 70° and a color saturation C value included between 20 and 50. The limit of this solution lies in the use of dyes absorbing the light and then producing a mat effect which cannot be corrected by the reflective particles described in these publications. Therefore, the luminosity of these compositions remains relatively weak and the skin color enlightenment effect unsatisfactory.

There is therefore a need for cosmetic compositions which ensure the enlightenment of the skin color without covering or opacifying the skin.

There is also another need for cosmetic compositions which ensure the enlightenment of the skin color without generating a gray or muddy coloring effect of the skin.

There is therefore another need for cosmetic compositions which ensure the enlightenment of the skin color along with a natural appearance of the skin color of complexion.

Furthermore, there is another need for cosmetic compositions which ensure the enlightenment of the skin complexion the perceived result of which is immediate.

There is therefore a need of reflecting systems that reflect light in the visible range, which the reflection intensity of which is high enough to make perceptible optically enlightenment of the skin and which are characterized by increased stability under natural light irradiation and chemical stability vis-à-vis the ingredients of cosmetic compositions containing them, in particular vis-à-vis a hydrophilic medium.

There further exists a need to be able to have available reflecting systems for improving the complexion of the skin, in particular its uniformity, promoting the optical enlightenment of the skin and for reducing defects of pigmentation of the skin.

There is also a need for reflecting systems for reducing a defect of pigmentation of the skin.

There is also a need for reflecting systems that are transparent enough to give the skin on which the cosmetic compositions containing them are applied non-opaque, clear and natural appearance but no covering appearance.

There is also a need for reflecting systems conferring intensity in color.

There is also a need that the effect of skin enlightenment is immediately perceived, is persistent over time and provides a flexible color tone to be chosen depending on the different types of treated skin.

There is also a need to benefit from three-dimensionally ordered macroporous inorganic structures or inverse opals that can be used to obtain optically enlightenment of the human keratinous material and that do not lose their optical properties and efficacy when applying them to keratinic materials via cosmetic compositions, in particular comprising a hydrophilic medium.

There is also a need to develop reflecting systems for achieving enlightenment of the human keratinous material without dulling.

There is also a need to develop reflecting systems that intensively reflect light when implemented within a cosmetic composition for an application to the keratin materials, in particular comprising a hydrophilic medium.

The invention aims to achieve all or some of these objects.

SUMMARY OF THE INVENTION

Unexpectedly, and as shown in the examples indicated below, the inventors have observed that the synthesized inorganic materials are able to give intense colored particles with high reflectance.

More specifically the inventors discovered that to produce ordered macroporous structures without loss of reflectance particularly in hydrophilic media, the formation of an additional layer comprising a hydrophobic property on the pore surface of the said structures, is very interesting. They further observed that said technique gives a color preservation without shift of the reflected wavelengths, and particularly in hydrophilic environments.

A first object of the present invention is directed to an inorganic material comprising particles of three-dimensionally ordered macroporous structure comprising spherical pores, said pores having an average pore diameter ranging from 50 nm to 10 μm, the pore diameter varying by no greater than 20%, the surface of said pores being coated by an absorber agent of the visible wavelength spectrum, said particles having an average largest dimension ranging from 1 to 50 μm, and wherein said particles are coated with at least a hydrophobic component.

The present invention further relates to a process an inorganic material comprising particles of in three-dimension ordered macroporous structure comprising spherical pores comprising the steps of:

(i) providing a colloidal crystal formed of a regular array of monodisperse organic polymer particles as a template, (ii) adding a material, in particular a precursor thereof, so as to produce a solid into the interstices between the monodisperse particles of the colloidal crystal and to form a solid continuous phase and a composite colloidal crystal thereof, wherein the material can optionally comprises at least one absorber agent of the visible wavelength spectrum and/or at least one precursor of a absorber agent of the visible wavelength spectrum, (iii) removing the monodisperse particles so as to form a regular array of pores in the solid continuous phase, and (iv) applying a coating onto the surface of the particles, said coating comprising at least one hydrophobic component.

The present invention further relates to a cosmetic composition comprising at least one inorganic material according to the present invention.

The present invention is additionally directed to the use of an inorganic material according to the present invention for obtaining enlightenment of the skin, homogenizing the complexion and/or reducing the defects of pigmentation of the skin.

According to yet another of its aspects, it is targeted at a cosmetic method for obtaining an enlightenment, and in particular optically enlightenment of the skin, for homogenizing complexion and/or reducing the defects of pigmentation of the skin, comprising at least one stage of applying to the skin a cosmetic composition according to the present invention.

DESCRIPTION OF THE PREFERRED EMBODIMENTS

In the framework of the present invention the following terms

"three-dimensionally ordered macroporous structure" means a structure where the pores are arranged or form a regular periodic array within a solid continuous phase For the purposes of the present invention, the term "keratin material" is intended to cover the skin, mucous membranes such as the lips, the nails and the eyelashes. The skin and the lips, in particular facial skin, are most particularly considered according to the invention.

The term "room temperature" is intended to denote a temperature of about 25° C. It is set at atmospheric pressure (i.e. a pressure of $1.013 \times 10^5$ Pa), The "refractive index" is related to the interaction between a material and a propagating radiation within the material. Said refractive index cannot be measured directly. It can be calculated according to the formulae described in the publication of A. Stein and al., Materials Views, 2010, 20, 2565-2578.

Reflectance may however be measured, which represents the ratio of the intensity of light reflected from the sample to the intensity of incident light, measured over a range of wavelengths. The method consist in depositing a thin film of transparent non scattering dispersant containing the material of the invention, the thickness of which being between 5 and 100 μm and to measure the reflectance with an integrating sphere according to the protocol based on LabSphere's technical guide as available on the following url: http://woodall.ece.ucdavis.edu/pdf/labsphere_reflectance_manual.pdf.

"defects in pigmentation" which may be reduced by application of a composition comprising inorganic macroporous material according to the present invention, are more particularly defined hereinafter.

Defects in pigmentation of the skin are frequent and can occur in a variety of different forms. However, the defects in skin pigmentation with which the invention is concerned can be defined as involving the appearance of at least one skin region having a darker or lighter color than the average color of the skin surface of the individual examined. This region can be macroscopic or microscopic in size.

Within the meaning of the invention, the term "defects in pigmentation of the skin" is understood to mean any event of appearance of a change in the color or in the complexion of all or part of the surface of the skin, which encompasses an overall or local change in the complexion of the skin, and also hyperpigmentation, hypopigmentation or dyspigmentation defects.

Within the meaning of the invention, the term "hyperpigmentation defect of the skin" is understood to mean any event of appearance of a skin region affected by an excess of pigmentation, in comparison with the average level of pigmentation of the skin surface of an individual.

Preferably, the level of pigmentation of a skin surface is measured using an appropriate standard color chart. For the measurement of the level of pigmentation, the standard color chart is applied to the skin so that at least one edge of said chart is placed beside the skin region to be measured. The value of degree of color on the chart which is the closest to the color of the skin region which is analyzed is recorded by visual comparison.

The defects of pigmentation of the skin can be marked by the presence of more or less extensive surface skin blemishes, having a darker or lighter color than the normal color of the skin of the individual which surrounds said skin blemishes.

The defects of pigmentation of the skin encompass in particular melasma and lentigines, including liver spots and actinic lentigo.

Melasma (also known as chloasma) is most frequently encountered in pregnant women and in women taking antiovulatory medicaments. Melasma is also known as "mask of pregnancy". Melasma appears as a broad dark reticular macula with uneven edges which is found mainly on the cheeks, upper lip and forehead. Melasma is also encountered in men or women not suffering from detectable endocrine imbalance, but exposure to the sun is necessary for its development.

In particular, the melasma or chloasma considered by the invention can be triggered by exposure to UV rays, or can occur on photosensitive skin, photoallergic skin or skin subject to a phototoxicity reaction.

Lentigines arise in the form of hyperpigmented skin blemishes which can appear at any age and are usually darker and more extensive than freckles. A lentigo is characterized in particular by an increase in the number of melanocytes in the basal layer. Lentigines encompass in particular (i) solar lentigines, which appear in light-skinned individuals on skin regions exposed for a long time to the sun, (ii) lentiginous pigmentation resulting from skin therapies involving UV-A radiation (320-400 nanometers—also known as PUVA therapy), (iii) multiple lentigines, especially on the palms, soles of the feet, mucous membranes or unexposed skin, or also (iv) lentigines affecting the lips, vulva or penis.

Defects of pigmentation of the skin also encompass hyperpigmentation situations resulting from inflammation or scarring. Postinflammatory hyperpigmentation is quite independent of the degree of inflammation and depends more on the nature of the trauma which brought about the inflammation. Postinflammatory hyperpigmentation can be severe after certain lesions, such as thermal burns or of acne type, or resulting from insect stings, cuts and other mechanical traumas of the skin, in particular during shaving, and pseudofolliculitis due to body hairs becoming ingrown as a result of shaving or depilation. Postinflammatory hyperpigmentation can persist for months, indeed even for years.

The defects of pigmentation of the skin targeted by the invention also concern the dyspigmentations resulting from a dysfunctioning of the metabolism of the melanocytes of the skin. Mention may be made, as examples of dyspigmentations targeted by the invention, of vitiligo, pityriasis versicolor or depigmentations due to burns or to surgery, the aftereffects of spots due to acne, and postshaving cuts.

A defect of pigmentation of the skin more particularly considered by the invention can be chosen from melasma, chloasma, lentigines, liver spots, vitiligo, postinflammatory hyperpigmentations due to an abrasion and/or a burn and/or a scar, genetically-determined hyperpigmentations, hyperpigmentations of metabolic or drug origin, or any other pigmentation lesions.

The present invention can also be employed to reduce the mask of pregnancy.

Inorganic macroporous material according to the present invention can more particularly be employed for obtaining optically enlightenment of the skin.

The present invention also relates to esthetic disorders of the skin affecting the complexion of the skin.

Thus, the invention may suitably be employed to reduce a lack of uniformity in the complexion of the skin.

The invention advantageously makes it possible to promote and maintain the radiance of the complexion of the skin and in particular a uniform complexion.

According to one embodiment, an inorganic macroporous material according to the invention can make it possible to confer, on the skin, a uniform, luminous, more radiant, indeed even more glowing, complexion indicative of skin in good health.

The invention advantageously makes it possible to reduce a muddy skin complexion, a lifeless skin complexion, a nonuniform skin complexion or imperfections of the skin chosen in particular from spots, dry patches, dyschromias or blackheads or also to prevent, reduce and/or treat a waxen, sallow, grayish or ashen, indeed even sickly, complexion.

According to one embodiment, the present invention can relate more particularly to colored skin.

The present invention relates to the entire surface of the skin of an individual. In particular, the present invention can advantageously be employed with regard to the skin of the hands, face or neckline.

Particles

The inorganic material according to the present invention comprises particles of a three-dimensionally ordered macroporous structure comprising a solid phase with spherical pores.

Said particles have an average largest dimension, also called size in the present invention, that advantageously ranges from 1 to 40 µm, preferably from 1 to 30 µm, and in particular from 5 to 10 µm.

It has been discovered that the range of the particle sizes is determining in order to get a high reflectivity and vividness.

The particles according to the present invention have a polymorphic shape.

The inorganic material is more particularly detailed hereinafter.

The pores present a spherical shape. The pores are arranged in the inorganic structure so as to have a substantially regular or constant spacing there between. However, as the skilled person could appreciate, some defects in the inverse crystal or inverse opals are unavoidable.

The pore diameter has a direct impact on the reflectance and is connected to the nature of the inorganic material as detailed below.

The "average pore diameter" means the mean pore diameter. It may be measured by Scanning Electron Microscopy (SEM) for instance.

The average pore diameter may range between 50 nm and 1 µm, in particular between 0.1 µm and 0.8 for example between 0.2 and 0.6 µm.

The distribution of the pores diameter is so that 90% of the pores of the whole particles present a diameter not greater than or lesser than 10% with respect to said average pore diameter, more particularly not greater or lesser than 8%, and even not greater or lesser than 5%.

In other words, the present invention relates to a "uniform" macroporous structure, i.e. encompassing pores that have substantially the same diameter. This means that the pore diameter in the framework of the present invention is preferably monodisperse or else that the pore diameter varies by no greater than 20%, preferably than 16% and even more preferably than 5%.

The surface of the inorganic material and the internal surface of the pores are recovered by an absorber agent of the visible wavelength spectrum, the visible wavelength ranging from 400 to 700 nm, as detailed below.

Said particles are coated on their surface with a hydrophobic component as described herein after.

The particles have preferably a full volume fraction calculated from 1% to 20%.

The method of calculation is disclosed in the article "Tuning solvent-dependent color changes of three-Dimensionally ordered macroporous (3DOM) materials through compositional and geometric modifications" Blanford and al, *Advanced Materials,* 2001, 13, 1, 26-29.

Inorganic Material

The inorganic material may be selected from metal oxides of metal having valency between 1 and 6. The metal may be chosen in the group consisting in titanium, iron, copper, magnesium, calcium, barium, aluminum, zinc, zirconium, strontium, silicon (Si), tin, bismuth, cerium or their alloys such as $TiO_2$, $Fe_2O_3$, $Al_2O_3$, CuO, ZnO, $ZrO_2$, MgO, CaO, BaO $Ba_2O_3$, $In_2O_3$, $SiO_2$, $SnO_2$, $Bi_2O_3$, $CeO_2$, $SrO_2$, $BaTiO_3$, $Bi_4Ti_3O_{12}$, $Bi_{12}SiO_{20}$, $Si_xO_y$, where x and y range independently from one another between 0.1 and 2.

According to a particular embodiment, the metal is in particular selected from titanium, iron, copper, magnesium, calcium, barium, aluminium, zinc, zirconium, strontium, silicon, tin, bismuth, cerium or one of their alloys such as $TiO_2$, $Fe_2O_3$, $Al_2O_3$, CuO, ZnO, $ZrO_2$, MgO, CaO, BaO, $SiO_2$, $CeO_2$, $BaTiO_3$, $Si_xO_y$ with x and y comprised independently from another between 0.1 and 2, and the metal being more particularly selected from $TiO_2$, $Al_2O_3$, ZnO, MgO, CaO and $Si_xO_y$ with x and y comprised independently from another between 0.1 and 2.

According to a more particular embodiment, the inorganic material is selected from $SiO_2$, $TiO_2$, $Al_2O_3$, even more selected from $SiO_2$ and $TiO_2$, and even more particularly is $SiO_2$.

The inorganic material, which represents the solid continuous phase, may be present in an amount from 50 to 98%, preferably from 75 to 98%, and most preferably from 85 to 98% by weight relative to the total weight of the particles.

Absorber Agent

The "absorber agent" is a compound that absorbs substantially the light having a wavelength in a range from 400 to 700 nm Said absorber agent appears black or darkly colored to human eye.

Because of the way of the production of the inorganic macroporous structure of the present invention the absorber agent should be able to bear the reaction condition of the production procedure. Depending on what kind of conditions is chosen the absorber agent should be suitable to bear temperature up to 1000° C. In the light of the present invention the term "absorber agent" also comprises a mixture of compounds wherein that mixture has the same absorption property as a single absorber agent. Therefore, in the following the term "absorber agent" always stands for either a single compound or a mixture of compounds.

It is also possible to use a precursor of an absorber agent. That precursor is converted into the absorber agent by using a form of energy (such as light (UV), heat, etc). That means that the precursor can be transformed during the production of the macroporous structure or after its production.

Suitable precursors for the present invention are metal salts, preferably hydrophilic metal salts, such as nitrates or halides. Preferred halides are F, Cl or I, whereas Cl is the most preferred halide.

The metals are for example alkaline metals, noble metals, or transition metals. Suitable metals are for example Sr, Zn, Fe, Ce, Co, Cu, Mn, Sn, Al, and Ag. Preferred are Ca, Mg, Al, Ag and Zn.

Very suitable metal salts are Ag nitrate, Ag halides, Fe nitrate and Fe halides (especially FeCl$_2$ and FeCl$_3$).

It is also possible to use more than one precursor.

As a further example FeCl$_2$ as well as FeCl$_3$ are converted into black iron oxide and/or iron hydroxide.

The absorber agent may be selected from polyphenols, melanines, eumelanines, aromatic azomethines, heteroaromatic azomethines, carbon black, black metallic oxides such as copper oxide (II), iron oxide(II) and silver oxide(I).

According to a particular embodiment of the present invention, the absorber agent is carbon black. In such a case, as it will be more apparent from the following description of the manufacturing process and the examples, it may be formed during a pyrolysis step of organic polymeric spheres used as a template for the formation of the pores.

The amount of the absorber agent, and in particular the carbon black, presents an influence on the reflectance.

According to a particular embodiment, the absorber agent is present in the particles in an amount ranging from 1 to 20% by weight, in particular from 2 to 15%, and preferably from 3 to 10% by weight relative to the total weight of the particles without the hydrophobic coating.

Hydrophobic Component

The hydrophobic component must coat the inorganic material on its internal and external surface. "Coat" means that a thin film of the hydrophobic component is deposited onto the surface of the inorganic material.

The "coating" or "surface finishing" then encompasses a surface treatment affecting partially or entirely the surface of the particles to confer hydrophobic properties, and namely the external surface of the particles and internal one, i.e. the internal surface of the pores within the particles.

According to a particular embodiment, the hydrophobic component is a polyorganosiloxane.

According to a more particular embodiment, the polyorganosiloxane presents the following units (I)

wherein (n,p,q) is (1,0,0); (1,1,0) or (1,1,1),

R$^1$, R$^2$ and R$^3$ radicals independently represent a hydrogen atom, a linear, or branched, saturated or unsaturated (C$_1$-C$_{26}$)alkyl radical, optionally interrupted by one to several (notably one to 4) oxygen atoms, and optionally substituted by one to several (notably one to 4) radicals selected from the group Gp$_1$, an aryl radical optionally substituted by one or several (notably one to 2) radicals selected from the group Gp$_2$, or a heteroaryl radical optionally substituted by one or several (notably one to 2) radicals selected from the group Gp$_2$, Gp$_1$ consists of a halogen atom, a OR$_4$ radical, a NR$_5$R$_6$ radical, a (C$_1$-C$_4$)alcoxycarboxyl radical, —COOR$_4$, a carboxamido —CONR$_4$R$_8$ radical, a thiol radical, a sulfonic —SO$_3$H radical, an aminosulfonyle radical —SO$_2$—NH$_2$, a dialkylaminosulfonyl —SO$_2$NR$_5$R$_6$ radical, a (C$_1$-C$_4$)alkylsulfonyl radical —SO$_2$-alkyl, a (C$_1$-C$_4$)alkylsulfoxyde radical —SO-alkyl, and a (C$_1$-C$_4$)alkylsulfonamido radical alkylNH—SO$_2$—, Gp$_2$ consists of a halogen atom, a C1-C4 alcoxy OR$_4$ radical, a carboxy radical, a carboxamido radical, a (C$_1$-C$_4$) alkylsulfonyl radical, a (C$_1$-C$_4$)alkylsulfonamido radical and a NR$_4$R$_5$ radical, R$_4$ represents a linear or branched (C$_1$-C$_4$)alkyl radical, optionally substituted by one or two (C$_1$-C$_2$)alcoxy radicals, R$_5$ and R$_6$ independently represent a linear or branched (C$_1$-C$_8$)alkyl radical, optionally interrupted by one or several (notably one to 4) oxygen atoms, and optionally substituted by one or several (notably one to 4) radicals selected from the group consisting of a OR$_4$ radical, a NR$_7$R$_8$ radical, a (C$_1$-C$_4$)alcoxycarbonyl radical —COOR$_4$, a halogen atom, a CONR$_7$R$_8$ radical, a SO$_2$NR$_7$R$_8$ radical, a aryl radical, optionally substituted by one or several (notably one to 2) radicals selected from the group Gp$_2$, a heteroaryl radical, optionally substituted by one or several (notably one to 2) radicals selected from the group Gp$_2$, R$_7$ et R$_8$ independently represent a linear or branched (C$_1$-C$_8$)alkyl radical, optionally interrupted by one or several (notably one to 2) oxygen atoms, and optionally substituted by one or two radicals selected from OR$_4$ radicals, R$_5$ and R$_6$ can form with the nitrogen atom to which they are attached, a heterocycle, optionally substituted by one or several radicals selected form the group Gp$_3$, said heterocycle not including a O—O group, nor a diazo or a nitroso group, and Gp$_3$ consists of halogen atoms, a amino radical, a di(C$_1$-C$_4$)alkylamino radical, a hydroxy radical, a carboxyl radical, a carboxamido radical, a (C$_1$-C$_2$)alcoxy radical, a (C$_1$-C$_4$) alkyl radical, optionally substituted by one or two hydroxy radicals, a amino radical, a di(C$_1$-C$_4$)alkylamino radical, a (C$_1$-C$_4$)alcoxy radical, a carboxyl radical, and a (C$_1$-C$_4$) alkylsulfonyl radical.

In the context of the present invention, the term:
"halogen" is understood to mean chlorine, fluorine, bromine, or iodine, and in particular denotes chlorine, fluorine or bromine, "(C$_1$-C$_x$)alkyl" as used herein respectively refers to C$_1$-C$_x$ containing hydrocarbon chain. Examples are, but are not limited to, methyl, ethyl, 1-propyl, 2-propyl, "(C$_1$-C$_x$)alcoxy" as used herein respectively refers to O—(C$_1$-C$_x$)alkyl moiety, wherein (C$_1$-C$_x$)alkyl is as defined above. Examples are, but are not limited to, methoxy, ethoxy, 1-propoxy, 2-propoxy, "heterocycle" as used herein respectively refers to a saturated or unsaturated cycle comprising between 5 and 7 carbon atoms, at least one atom in the group consisting of nitrogen, oxygen or sulfur atoms, and optionally comprising between 1 and 3 additional heteroatoms, such as oxygen, nitrogen or sulfur. Mention may be made especially of piperidyl, piperazinyl, pyrrolidinyl, pyrazolidinyl, morpholinyl, imidazolyl, thiazolyl, pyrrolyl, oxazolyl, pyrazolyl and pyridinyl groups.

The term "aryl" refers to a mono or polycyclic aromatic hydrocarbon radical of 6-20 atoms. Typical aryl groups include, but are not limited to 1 ring or 2 or 3 rings fused together. Said radical is typically selected from phenyl, naphtyl, anthracenyl, and the like. "Aryl" preferably refers to phenyl.

The term "heteroaryl" denotes a heterocyle, as mentioned above, used as substituent of an atom.

According to an even more particularly preferred embodiment, the polyorganosiloxane presents the following units (I)

wherein (n,p,q) is (1,0,0); (1,1,0) or (1,1,1),

R$^1$, R$^2$ and R$^3$ radicals independently represent a hydrogen atom, a linear or branched, saturated or unsaturated (C$_1$-C$_{26}$)alkyl radical, optionally interrupted by one to four oxygen atoms, and optionally substituted by one to four radicals selected from the group Gp$_1$, an aryl radical optionally substituted by one or two radicals selected from the group Gp$_2$, Gp$_1$ consists in a OR$_4$ radical, a (C$_1$-C$_4$)alcoxycarboxyl radical —COOR$_4$, Gp$_2$ consists in a OR$_4$ radical or a carboxy radical, R$_4$ represents a (C$_1$-C$_4$)alkyl radical eventually substituted by one or two (C$_1$-C$_{26}$)alcoxy radicals.

According to the preceding definition of the polyorganosiloxane, it comes out that it may be silicone oil (which may be volatile or non volatile silicone oil), a silicone elastomer or even a silicone resin, and a mixture thereof.

Among silicone oils, one may cite cyclic or linear silicones, preferably with a viscosity at room temperature and at atmospheric pressure of less than 8 cSt, and in particular having from 2 to 7 silicon atoms, such as preferably octamethylcyclotrasiloxane, decamethylcyclopentasiloxane, hexadecamethylcyclohexasiloxane, heptamethylhexyltrisiloxane or heptamethyloctyltrisiloxane.

Silicone oils may also be chosen among polydimethylsiloxanes (PDMS), phenylated polyorganosiloxane, such as phenyltrimethicones, phenyl dimethicones, trimethylsiloxyphenyl dimethicones, phenyl trimethylsiloxy diphenylsiloxanes, diphenyl dimethicones, diphenyl methyldiphenyl trisiloxanes, polysiloxanes modified with fatty acids, with fatty alcohols or with polyoxyalkylenes, mixtures thereof.

Among silicone elastomers one may cite Dimethicone crosspolymer (INCI name), vinyl dimethicone crosspolymer (INCI name), Dimethicone/vinyldimethicone crosspolymer (INCI name), Dimethicone crosspolymer-3 (INCI name). Such silicone elastomers are disclosed in the documents EP242219, EP285886, EP765656, JP-A-61-194009.

Among silicone resin (which are tridimensional organosiloxanes), one may cite MQ type resins, T type resins such as polysilsesquioxanes, MQT type resins.

The glossary of silicone resin is known under the name "MDTQ", depending of the different monomeric unities present, each letter "MDTQ" corresponding to a unity type.

The letter «M» is the Monofonctional unit of formula R1R2R3SiO$_{1/2}$, in which the silicon atom is linked to only one oxygen atom in the polymer containing this unity.

The letter «D» is the Difonctional unit R1R2SiO$_{2/2}$ in which silicon atom is linked to two oxygen atoms.

The letter «T» is the Trifonctional unit of formula R1SiO$_{3/2}$.

Such resins are described for example in «Encyclopedia of Polymer Science and Engineering, vol. 15, John et Wiley and Sons, New York, (1989), p. 265-270, and U.S. Pat. Nos. 2,676,182, 3,627,851, 3,772,247, 5,248,739, 5,082,706, 5,319,040, 5,302,685 et U.S. Pat. No. 4,935,484.

According to a particular embodiment, said silicone resins present a melting point of less than 80° C., preferably of less than 50° C.

The melting point of the resin can be measured by means of a differential scanning calorimeter (DSC), for example the calorimeter sold under the designation DSC 30 by the company METLER.

The measurement protocol is as follows:

A 15 mg sample of product in a crucible is submitted to a first temperature rise from 0° C. to 120° C., at a heating rate of 10° C./minute, then it is cooled from 120° C. to 0° C. at a cooling rate of 10° C./minute and is finally submitted to a second temperature rise from 0° C. to 120° C. at a heating rate of 5° C./minute. During the second temperature rise, the variation of the difference in power absorbed by the empty crucible and by the crucible containing the sample of product is measured as a function of temperature. The melting point of the compound is the temperature value corresponding to the top of the peak of the curve representing the variation of the difference in power absorbed as a function of temperature.

The polyorganosiloxane may of course be a mixture of the preceding cited polyorganosiloxanes.

According to a particular embodiment, the hydrophobic component is PDMS.

The number-average molecular weight of PDMS may typically range between 400 g/mol and 150000 g/mol, in particular between 500 g/mol and 30000 g/mol, for example between 2000 g/mol and 10000 g/mol.

The number-average molecular weights (Mn) are determined by gel permeation liquid chromatography (THF solvent, calibration curve established with linear polystyrene standards, refractometric detector).

Said PDMS may be selected from "Liquid Wrench Silicone Spray" sold by Radiator Speciality Company.

The hydrophobic component may be present in an amount ranging from 1% to 30% by weight, in particular from 1% to 10% by weight, for example from 1 to 5% by weight, with respect to the total weight of the particles.

Manufacturing Process

According to the present invention, the manufacturing process implements organic polymer templates for the formation of the pores within the inorganic structure.

Such a process is for example described in U.S. Pat. No. 6,680,013.

As a far as the color of the particles is concerned, it depends on the diameter of the pores within the macroporous structure.

Moreover, depending on the chemical nature of the inorganic material of the particles, the pore diameter d is calculated according to the physical rules established in the literature ("Optical Properties of Inverse Opal Photonic Crystals" Schroden and al, Chem. Mater. 2002, 14, 3305-3315) so as to predetermining the range of visible wavelength the particles should reflect. A range of monodisperse organic polymer spheres is defined from this criterion with different diameters, these diameters being within an interval [d; 1,3.d].

Processes for making macroporous structures are known. For example, an inverse colloidal crystal may be formed by conducting the steps of:

(i) providing a colloidal crystal formed of a regular array of monodisperse organic polymer particles as a template, (ii) adding a material, in particular an inorganic material or a precursor thereof, so as to introduce a solid into the interstices between the monodisperse particles in the colloidal crystal and to form a solid continuous phase or composite colloidal crystal, wherein the material comprises at least one absorber agent and/or at least one precursor of a absorber agent; and (iii) removing the monodisperse particles so as to form a regular array of pores in the solid continuous phase.

Each of said steps may be performed according to known methods.

The process according to the present invention contains an additional step (iv) which consists in an hydrophobization step.

Said step in particular consists in the application of a coating on the surface of the particles, said coating comprising at least one hydrophobic component.

Steps (i), (ii), (iii) and (iv) are more particularly detailed herein below.

Step (i): Formation of the Colloidal Crystal

The colloidal crystal can be formed from monodisperse organic particles as a template.

Such monodisperse particles are commercially available or can be prepared by methods known in the art.

Monodisperse particles made from organic polymer particles may be prepared as dispersions using emulsion, dispersion or suspension polymerization.

Suitable hydrophobic monomers include styrenics, acrylonitrile, methacrylonitrile, acrylates, methacrylates, methacryl amides, acrylamides, maleimides, vinyl ethers, vinyl esters, monoalkylmaleates, dialkyl maleates, fluorinated acrylates and fluorinated methacrylates.

Examples of preferred organic polymer particles include polystyrene spheres, polymethyl methacrylate spheres, and the like. Such particles are commercially available from sources such as Polysciences, Inc., Interfacial Dynamics Corp., and Duke Scientific Corp.

Monodispersed poly(methylmethacrulate) or PMMA may in particular be used as a template.

PMMA colloids may alternatively be prepared from monomer methylmethacrylate according to the protocol described in the literature ("Model Filled Polymers. V. Synthesis of Crosslinked Monodisperse Polymethacrylate Beads", Zou and al, *J. Polym Sci Part A* Polym Chem 1992, 30, 137). To ensure excellent monodispersity, the polymerization temperature may be set between 45 and 120, in particular between 60 and 100, and for example at 90° C. for the time necessary for consumption of methylmethacrylate. The monomer concentration may be between 1 and 2 mol $L^{-1}$, preferably between 1.3 and 1.8 mol $L^{-1}$.

As previously mentioned, the PMMA spheres may also be used to form carbon black, as an absorber agent as explained above.

It is also possible that a colloidal crystal is formed which comprises at least one absorber agent. In such a case it is possible that the absorber agent is added to the monodisperse particles during the formation of the crystal. So it is possible that the absorber agent and/or the precursor of an absorber agent is located on the surface of monodisperse organic polymer particles as well as it can be located between the monodisperse particles. But is also possible that the absorber agent is encapsulated in the monodisperse organic polymer particles.

All combinations of the possible location of the absorber agents and their precursors are possible as well.

The colloidal crystal template formed during this step (i) preferably is a close-packed array of spheres. As used herein, a close-packed array is an array in which the spheres are packed in the smallest volume possible without significantly distorting the shapes of the spheres. The colloidal crystal template can include defects (e.g., point, line, plane defects), typically in a relatively small number, if desired. The formation of such a template can be done by a variety of methods, such as centrifugation, sedimentation, spin coating, evaporation methods, layer-by-layer growth, crystallization in capillaries, deposition in lithographic patterns, and the like.

According to a particular embodiment, the colloidal crystal template is formed by centrifugation. In particular such a technique is efficient as allowing removing solvent from the space between spheres and allowing close-packing.

According to a particular embodiment, the step (i) comprises the formation of a colloidal crystal by centrifugation of a PMMA colloid suspension. Centrifugation speed may then be set between 500 tr·$min^{-1}$ and 8000 tr·$min^{-1}$, preferably between 800 tr·$min^{-1}$ and 3000 tr·$min^{-1}$. Centrifugation time may vary from 1 hour to 96 hours, preferably between 6 and 72 hours. The supernatant may then be removed and the colloidal crystal thus obtained may be placed in an oven at a temperature between 30 and 60° C. to obtain PMMA spheres ordered material.

The obtained colloidal crystal may then be dried during 1-2 days, at temperatures that may range between 30° C. and 60° C., typically between 40° C. and 50° C.

Step (ii): Formation of the Composite Colloidal Crystal

One or more inorganic precursors may be added to the colloidal crystal as obtained in step (i) in a manner that allows the precursor(s) to permeate the interstitial spaces between the particles, preferably, close-packed spheres.

The inorganic precursor can be a liquid, solid, or a gas. Typically, the precursor is a solid or liquid dissolved in one or more solvents in which one or more precursors are soluble. An inorganic precursor can be used without a solvent (i.e., neat) if it is a liquid with a sufficiently low viscosity that it can permeate the interstitial spaces. If necessary for the liquid precursors, a solvent can be used to adjust the viscosity and rate of penetration. If a solvent is used in an inorganic precursor composition, it can be water, an alcohol, or other organic solvent that is compatible with the organic polymer spheres. By this it is meant that the solvent does not dissolve the particles, but sufficiently wets them to allow for penetration throughout the interstitial spaces. The inorganic precursor composition can be added to the template by soaking the template in the composition, filtering the composition through the template, etc. Penetration of the interstitial spaces can occur simply by gravity flow, capillary action, or through the use of pressure differentials, for example, as in vacuum-assisted percolation. Preferably, the solvent and the method of penetration are selected to allow the inorganic precursor composition to penetrate the template and substantially eliminate faults in the final structure as a result of non-wetted regions.

The inorganic precursor impregnated into the colloidal crystal template may then be converted into a hardened inorganic framework around the organic polymer particles, thereby forming a composite material. This can occur through several steps and several mechanistic pathways, depending on the type of inorganic precursor.

In one embodiment, the inorganic precursor is an alkoxide. It will undergo hydrolysis and condensation reactions to produce an oxide and water (or alcohol), which can be further removed upon drying. This is referred to herein as a "sol-gel" process, and can optionally involve the incorporation of an acid or base catalyst (e.g., tetrapropyl ammonium hydroxide) into the inorganic precursor composition. This material can then be converted to the desired end-product by appropriate treatment methods.

Typically, in a sol-gel process, an alkoxide $(M-OR)_n$ undergoes hydrolysis (forming $M(OH)_x(OR)_{n-x}$), often acid- or base-catalyzed, and condensation (forming M-O-M bonds either through dehydration or dealcoholation) to form a sol that is then converted to a gel. A sol is a suspension or dispersion of discrete colloidal particles, whereas a gel is a polymeric solid containing a fluid component, which has an internal network structure such that both the solid and fluid components are highly dispersed. The gel can then be dried and calcined at an elevated temperature to form a more dense ceramic material in the framework. Typically, the conversion, including sol-gel formation and drying can occur at room temperature or upon the application of heat, e.g., a temperature of 25° C. to 1000° C., although this can depend on the precursor(s) used. The calcination is typically carried out at a temperature of 300° C. to 1000° C.

According to a particular embodiment, an aqueous-alcoholic solution of metal oxide precursor acidified with a mineral or organic acid may be infiltrated into the interstices of the colloidal crystal at a temperature between 5° C. and 50° C., preferably between 15° C. and 30° C. The concentration may be between 0.1 mol $L^{-1}$ and 3 mol preferably between 0.5 mol $L^{-1}$ and 1.5 mol $L^{-1}$.

Still according to this particular embodiment, after complete impregnation, excess precursor solution may be filtered and the colloidal crystal impregnated may be placed in a closed reactor. The polycondensation of the metal oxide precursor may be carried out at a temperature between 15° C. and 80° C., preferably between 20° C. and 30° C. for a period between 2 hours and 48 hours, preferably between 4 and 24 hours.

According to a particular embodiment, the precursor is a silica precursor and in particular is a tetraethylorthosilicate.

The inventors have discovered that the precursor quantity is governing the intensity of the color of the obtained particles.

According to a particular embodiment, the quantity of the precursor is chosen so that the average refractive index of the particles is greater than 1.1.

Step (iii): Formation of the Inverse Opal

The organic polymer particles of the colloidal crystal template can be removed either simultaneously with the conversion process of the precursor as described above or subsequent thereto. Typically, the template should not be removed until the material of the framework is in a sufficient state such that the macroporous structure does not collapse or significantly deteriorate with respect to pore size and shape, although some shrinkage is allowed. Template removal typically is achieved by either calcination (or pyrolysis) or by extraction. Preferably, at least about 80% by weight, more preferably, at least about 95% by weight, and most preferably, at least about 98% by weight, of the organic polymer spheres are removed from the composite material. There may, however, be carbon residue remaining within the pores. For example, as much as 40% by weight carbon can remain after calcination of the template particles in a non-oxidizing atmosphere. This carbon residue or carbon black advantageously plays the role of an absorber agent as explained above.

Calcination may typically be carried out at a temperature of 300° C. to 1000° C., in particular of 300° C. to 700° C., although this depends on the spheres used as a template and on the composition of the inorganic framework that is formed. The heating can for example take place in an oven. It may further be performed with specific levels depending on the nature of the metal oxide.

According to a particular embodiment, calcination is used to remove the organic polymer spheres.

According to a more particularly preferred embodiment, calcination under inert atmosphere is used to remove the organic polymer spheres.

Inert atmosphere may be obtained under argon or nitrogen.

It has indeed been observed that if calcination is performed under an oxidizing atmosphere, such as under an air flow, the obtained particles have a very low reflectance, or present a slightly tinted white. In contrast, under an inert atmosphere such as under nitrogen or argon, the reflectance of the obtained particles increases significantly so that their perceived color becomes intense.

It has additionally been observed that according to the temperature gradient in use, the intensity of the reflection light is further increased.

According to a particular embodiment, the temperature gradient is selected so that the generated carbon black content is between 1 and 15%, preferably between 2 and 5% with respect to the total weight of the particles without hydrophobic coating. A second parameter which governs the choice of the temperature gradient is the reduction of pore diameter in comparison to the diameter of the PMMA spheres. The calcination conditions should be determined so that the diameter reduction rate is constant.

The obtained particles, or aggregates of particles, present a size comprised between 0.8 and 500 μm. Therefore, in order to obtain particle sizes in conformity with the claimed range, i.e. 2 to 20 μm, offering intense colors, and the following further steps may be performed.

The obtained particles may then be dispersed in solvent, for example in an ethanol solution, then crushed and sieved to isolate particles of lower size than 20 microns. The particles thus obtained have a relatively intense color violet, blue, green, or red, the latter being governed by the size of the chosen organic colloid, in particular PMMA, spheres.

Thereafter, the obtained particles may be dispersed in a solvent, for example an ethanol solution, at a concentration of between 0.01 mol·$L^{-1}$ to 1 mol $L^{-1}$, preferably between 0.05 and 0.15 mol $L^{-1}$. After 24 to 48 hours, the supernatant may be removed by suction, and the obtained particles may be spinned, washed with ethanol and then dried in oven with a temperature ranging from 40 to 50° C. Size of the obtained particles may be between 5 and 10 microns. The obtained particles may be blue, green or red, each color being particularly intense.

Step (iv): Hydrophobization of the Obtained Particles

As mentioned above, forming a hydrophobic coat on the surface of the particles, including partially and including on the external and internal parts of the particles, i.e. pores of the macroporous structure, allows to preserve the color properties when the particles are suspended within a medium, and in particular a hydrophilic medium.

Due to the variety of polyorganosiloxane that may be used in the framework of the preparation of hydrophobic coated inorganic material, i.e. volatile oils, silicone elastomers and silicone resins, the hydrophobizing process may be adapted.

In particular, when the polyorganosiloxane is an elastomer or a silicone resin, an infiltration step may be implemented before the heating step.

Said infiltration step may be carried out at a temperature ranging from 30° C. to 150° C., in particular from 80 to 100° C.

The particles as obtained in step (iii) may be dispersed in an apolar solvent containing a hydrophobic component as described above. Said dispersion may occur at a concentration of between 0.01 and 1 mol $L^{-1}$ at room temperature, in particular between 0.1 and 0.5 This step is an impregnation step.

The hydrophobic component, and in particular polyorganosiloxane, may be fixed on the particles through a heating step.

After spinning, the impregnated particles may be placed in a furnace and heated to a temperature ranging from 100 to 800° C., in particular from 300 to 600° C., for example at 350° C.

This step steps allow a chemical linkage of the hydrophobic coating on the surface of the particles. As already mentioned, said coating recovers the surface of the particles, internal and external parts of them, in a complete or partial manner. The temperature may be raised with a gradient ranging from 20 to 800° C., in particular from 30 to 350° C., for example of 10° C.·$min^{-1}$, for example with a flow of inert atmosphere ranging from 0.1 to 3 L·$min^{-1}$, in particular from 0.5 to 1 L·$min^{-1}$, for example of 0.6 L·$min^{-1}$.

According to a particular embodiment, the heating step may be performed under inert atmosphere, for example under a nitrogen or argon atmosphere.

The isolated obtained particles have a very intense color reflection, without changing intensity and hue in hydrophilic environments.

Cosmetic Composition

According to one of its aspects, the present invention relates to a cosmetic composition comprising an inorganic material according to the present invention, in particular in an amount ranging from 0.1 to 30% by weight with respect to the total amount of the composition, in particular ranging from 0.1 to 30%, more particularly from 0.1 to 15%, and preferably from 0.5 to 10% by weight.

The cosmetic compositions according to the invention comprise a physiologically acceptable medium, i.e. a non-toxic medium that can be applied to human keratinic material, especially skin, and more particularly facial skin, and which is of pleasant appearance, odor and feel.

In particular, the cosmetic composition according to the present invention is dedicated for making up the skin, and more particularly facial skin.

The term "skin" is intended to denote all of the skin of the body, including the lips, and preferably the skin of the face, the neck and the neckline, and also the lips.

In particular, a cosmetic composition according to the invention may be any type of cosmetic composition such as a foundation, a face powder an eye shadow a concealer product, a blusher a lipstick, a lip balm, a lip gloss, a lip pencil, an eye pencil, an eyeliner, a mascara, a body makeup product, a skin coloring product, a care product such as a care cream, a tinted cream or an antisun product, preferably a foundation and even more preferably a liquid foundation.

The composition may comprise water, for example in a content ranging from 20% to 95% by weight, preferably ranging from 30% to 90% by weight and preferentially ranging from 40% to 70% by weight, relative to the total weight of the composition.

The composition may also comprise an organic solvent that is water-miscible at room temperature (25° C.), chosen especially from monoalcohols containing from 2 to 6 carbon atoms, such as ethanol or isopropanol; polyols especially containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol (C1-C4)alkyl ethers, and mono-, di- or triethylene glycol (C1-C4)alkyl ethers; and mixtures thereof.

The composition according to the invention may comprise a solvent that is miscible with water at room temperature, in a content ranging from 1% to 20% by weight and preferably ranging from 3% to 15% by weight relative to the total weight of the composition.

The composition could be in form of emulsion, oil-in-water emulsion, water-in-oil emulsion, aqueous gel.

In a known manner, the cosmetic composition of the invention may also contain adjuvants that are common in cosmetics, such as lipophilic gelling agents, preserving agents, advantageously saturated $C_2$-$C_5$ monoalcohols, fragrances, fillers, UV-screening agents, which are especially lipophilic, bactericides, odour absorbers, dyestuffs, plant extracts, antioxidants and nonionic, anionic, cationic or amphoteric surfactants.

The amounts of these various adjuvants are those conventionally used in the field under consideration, and are for example from 0.01% to 20% of the total weight of the composition.

According to a particular embodiment, a cosmetic composition comprises at least two different inorganic materials according to the present invention.

For example, a cosmetic composition may comprise at least two different organic materials independently reflecting in the blue domain and in the green domain, or independently reflecting in the green domain and in the red domain.

According to a further particular embodiment, a cosmetic composition comprises at least three different inorganic materials according to the present invention, i.e. independently reflecting in the blue domain, the green domain and the red domain.

The invention precisely allows considering all types of hue by mixing appropriate colored inorganic material according to the present invention and obeying to the additive rule of colors.

In the description and in the examples that follow, unless otherwise mentioned, the percentages are weight percentages and the ranges of values written in the form "between . . . and . . . " include the stated lower and upper limits.

The examples below are presented as non-limiting illustrations of the field of the invention.

EXAMPLES

Example 1: Blue Ordered Macroporous Particles (Particles P1)

1.1. Preparation of the PMMA Spheres

In a 3 L jacketed reactor vessel equipped with a stirrer anchor type, 285 g of methyl methacrylate are loaded, and then 1.7 L of water. The stirring is started under a nitrogen stream in the reaction medium. The temperature of the jacket is raised to 90° C. When the reaction temperature reaches 78° C. and stabilizes, the catalyst (1.5 g) is quickly introduced into solution in water. The nitrogen flow is stopped and then after almost 6 hours at 90° C., the reaction mixture is cooled to room temperature. The suspension is then filtered through cotton and a suspension of 1.5 L containing 18% of a spherical PMMA is obtained.

PMMA Spheres Characterization by Laser Diffraction or Static Light Scattering (SLS) with Malvern Hydro 2000

10 g of PMMA suspension is diluted in 100 g of water and said solution is used for measuring the average diameter of the particles.

The measured average diameter is of 321 nm+/−5 nm.

Figure 1:
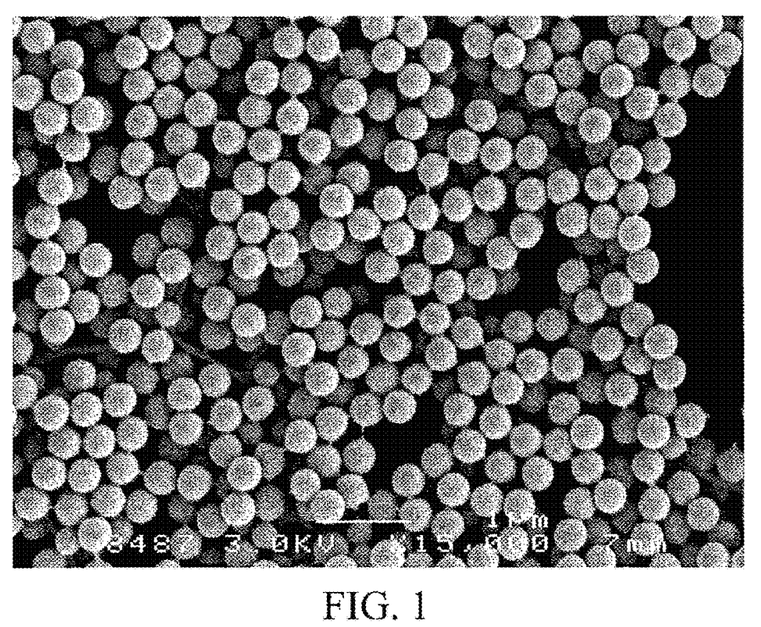
FIG. 1 represents an image of a PMMA suspension according to example 1.

FIG. 1 represents said PMMA suspension.

1.2. Colloidal Crystal Formation

PMMA colloid suspension is centrifuged at 1000 tr·mn$^{-1}$ for a period of 72 hours until the spheres are no more dispersed in the supernatant solution. The supernatant water is removed and the colloidal crystal is isolated and dried in oven at 30° C. to obtain 270 g of crystal.

Figure 2:
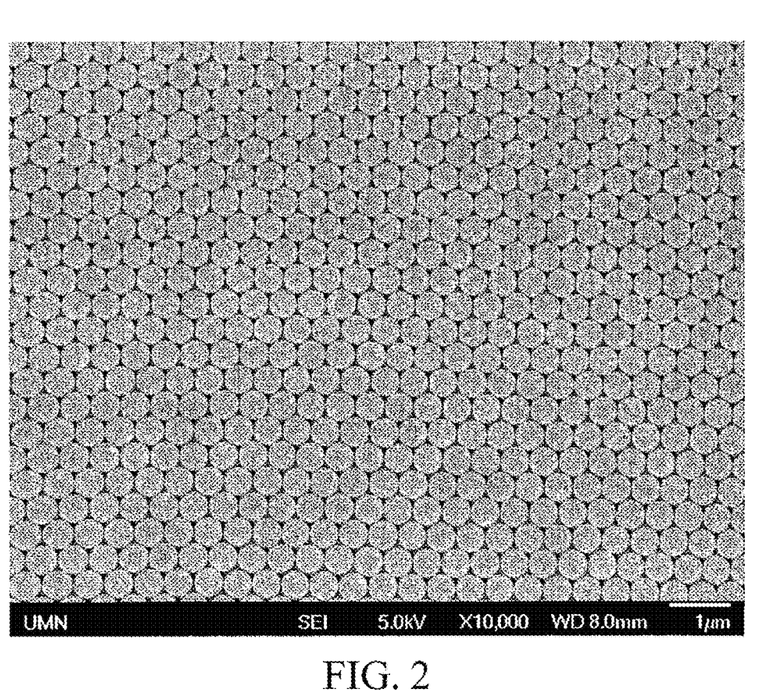
FIG. 2 represents an image of a colloidal PMMA crystal according to example 1.

Characterization by scanning microscopy: the obtained image shows that the cavities are perfectly aligned.

FIG. 2 represents said colloidal crystal.

1.3. Forming the Composite Colloidal Crystal

A solution containing 6 g of tetraethylorthosilicate, 4 mL of methanol and 3 mL of deionized water is placed in a 100 mL flask equipped with a thermometer and a magnetic stirrer. 1 g of concentrated hydrochloric acid 36N is added to this solution at room temperature. After the exothermic phase, the reaction medium is stirred until the temperature reaches 25° C.

Moreover, 15 g of colloidal crystal are arranged on a filter paper on a Buchner funnel. The silica precursor solution is dispersed in the colloidal crystal slowly, then wrung to remove excess solution. The infiltrated solid is recovered, transferred to an oven at 30° C. for 24 hours during which the polycondensation of the silica precursor is performed to yield 17 g of the composite.

Figure 3:
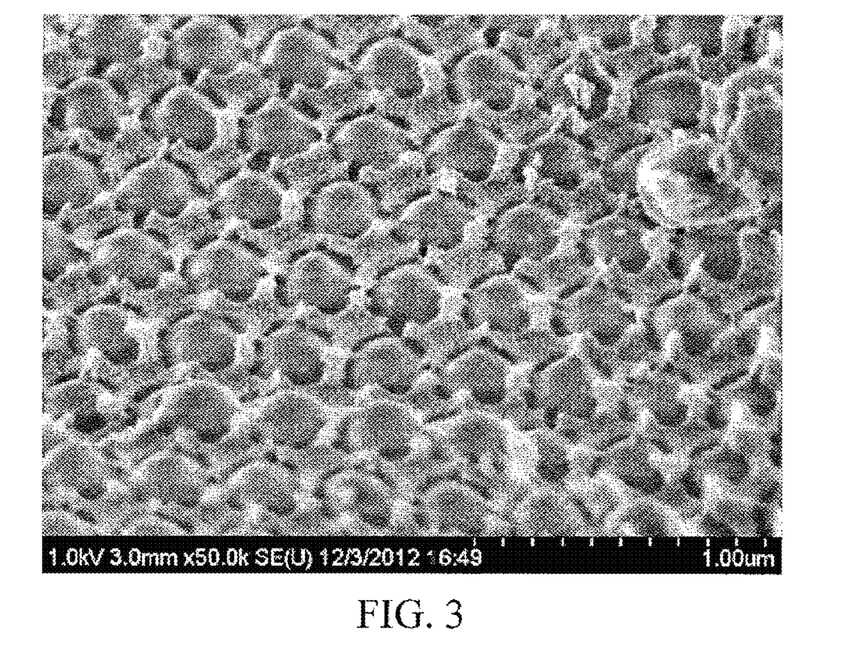
FIG. 3 represents an image of a composite colloidal crystal according to example 1.

FIG. 3 represents said composite colloidal crystal.

1.4. Formation of the Inverse Opal Silica 1.4.1. In an oven equipped with an atmosphere control, 3 g of composite as obtained at the preceding step are placed in a calcining tube wherein a stream of nitrogen is flowing. Under a nitrogen flow of 0.6 L·mn$^{-1}$, the temperature is raised to 500° C. at 5° C.·min$^{-1}$ to 500° C., then 700° C. for 2 hours. After furnace cooling, the solid is collected to yield 0.46 g of inverse opal with a blue color. The solid is then dispersed in ethanol after having spread on a sieve of 20 microns, then passed through the sieve. The ethanol suspension containing the particles of inverse opal stands for 24 hours at room temperature. After removing the supernatant, the solid is again dispersed in 10 ml of ethanol and the suspension is allowed to settle. After 24 hours, the supernatant is removed and the solid placed in an oven at 100° C. to constant weight to obtain 0.4 g of powder of very intense blue color.

Pore size of the obtained material is 288 nm as measured by SEM and the full volume fraction calculated at 4.5%.

The maximum reflection is obtained at a wavelength of $\lambda$max=480 nm by measuring diffuse reflectance with an Integrating Sphere RT-060-SF LabSphere.

1.4.2. In an oven, 3 g of composite as obtained at the preceding step are placed in a calcination tube wherein a stream of air is flowing. Under an air flow of 0.6 L·min-1, the temperature is raised to 500° C. at 5° C. min$^{-1}$ to 500° C. After furnace cooling, the solid is collected to yield 0.42 g of inverse opal with a pale blue color. The solid is then impregnated with a solution containing 5 w/w of sucrose, and then placed in a furnace where a stream of nitrogen is flowing like in the step 4.1.1. After collection of the calcinated solid, the solid is then dispersed in ethanol after having spread on a sieve of 20 microns, and then passed through the sieve. The ethanol suspension containing the particles of inverse opal stands for 24 hours at room temperature. After removing the supernatant, the solid is again dispersed in 10 ml of ethanol and the suspension is allowed to settle. After 24 hours, the supernatant is removed and the solid placed in an oven at 100° C. to constant weight to obtain 0.38 g of powder of very intense blue color.

1.5. Processing of the Inverse Opal by a Polydimethylsiloxane

In a 50 mL beaker, 0.4 g of material as obtained above are infiltrated with a solution of polydimethylsiloxane "Liquid Silicone Wrench Spray" sold by Radiator Speciality Company. Silicone infiltrated powder is placed in a furnace under a nitrogen stream of 0.6 L·mn$^{-1}$ and the temperature raised to 500° C. at 20° C.·mn$^{-1}$ After furnace cooling, the particles P1 are isolated to obtain an intense blue powder.

The obtained particles have an average largest dimension of about 6 μm.

Figure 4:
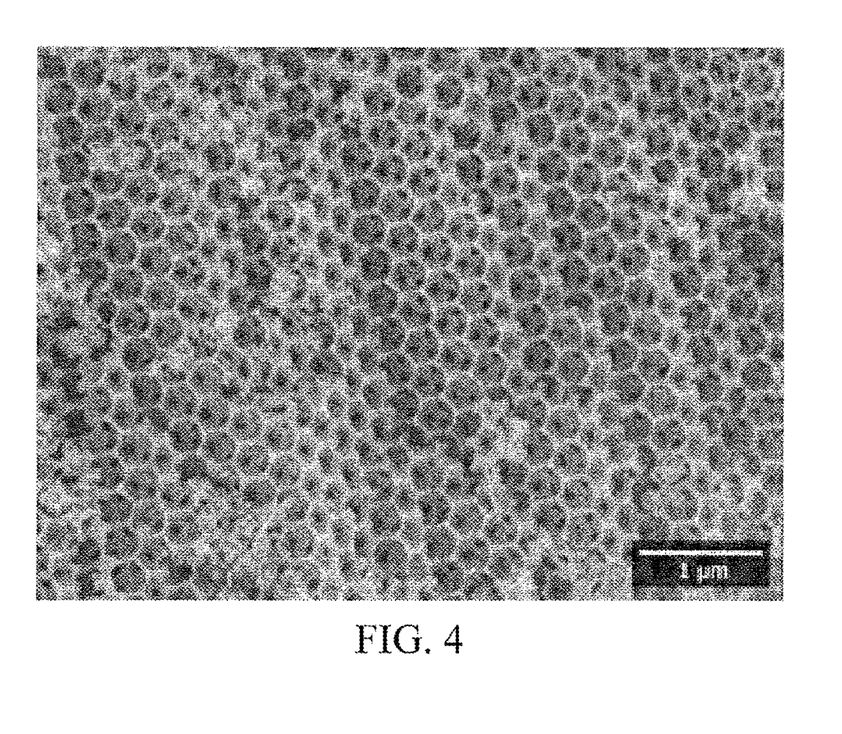
FIG. 4 represents a SEM image of the inverse opal as obtained in example 1.

A SEM image allows verifying the ordered structure of the material, with pores perfectly aligned and allows verifying the required pore diameter distribution, i.e. a homogeneous pore diameter.

FIG. 4 represents said SEM image of the obtained inverse opal.

Example 2: Green Ordered Macroporous Inorganic Particles (Particles P2)

Preparing P2 particles takes place according to a protocol similar to that used for the preparation of the particles P1.

The size of the PMMA spheres is fixed at 410+/−5 nm.

The diameter of the pores of the isolated P2 particles material is 336 nm+/−5 nm.

The full volume fraction is calculated as 2.1% and the maximum reflection is obtained at a wavelength of $\lambda$max=554 nm by measuring diffuse reflectance.

The obtained particles have an average largest dimension of about 6 nm.

Figure 5:
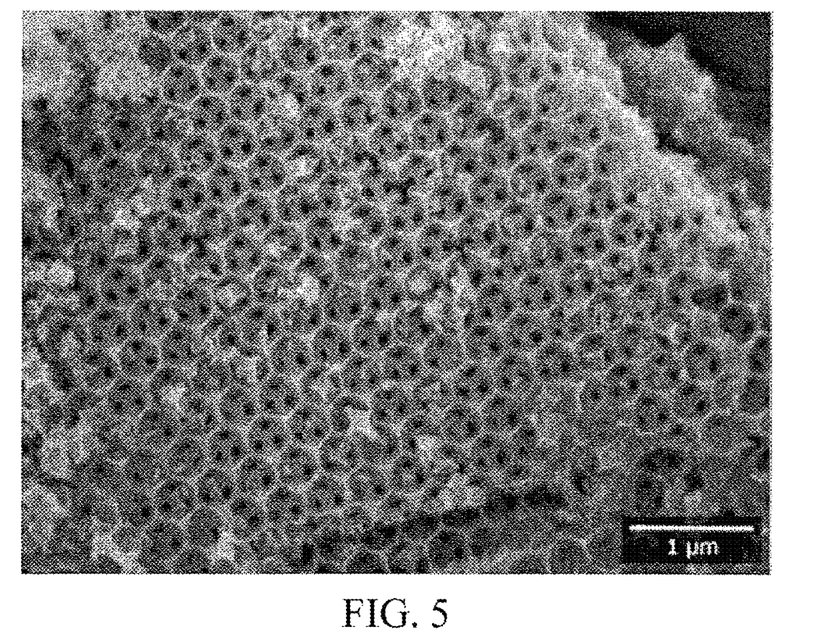
FIG. 5 represents a SEB image of the inverse opal as obtained in example 2.

A SEB image allows verifying the ordered structure of the material, with pores perfectly aligned and allows verifying the required pore diameter distribution, i.e. a homogeneous pore diameter.

FIG. 5 represents said SEB image.

Measurements

The corresponding reflectance measurements were carried out on a detector diode spectrophotometer Hewlett Packard 8452A for illustrating the color intensity variation depending on the calcination temperature of particles P2.

| | Calcination temperature | | | | |
|---|---|---|---|---|---|
| | 475° C. | 500° C. | 550° C. | 650° C. | 700° C. |
| Reflectance (%) | 19% | 17% | 14% | 11% | 10% |
| | $\lambda_{max}$ 566 nm | $\lambda_{max}$ 563 nm | $\lambda_{max}$ 559 nm | $\lambda_{max}$ 546 nm | $\lambda_{max}$ 538 nm |

Example 3: Red Ordered Macroporous Particles (Particles P3)

Preparing P3 particles takes place according to a protocol similar to that used for the preparation of the particles P1.

The size of the PMMA spheres is fixed at 480+/−5 nm.

The diameter of the pores of the isolated P3 particles material is 360 nm+/−5 nm.

The full volume fraction is calculated as 12.0% and the maximum reflection is obtained at a wavelength of $\lambda$max=626 nm by measuring diffuse reflectance.

The obtained particles have an average largest dimension of about 6 nm.

Figure 6:
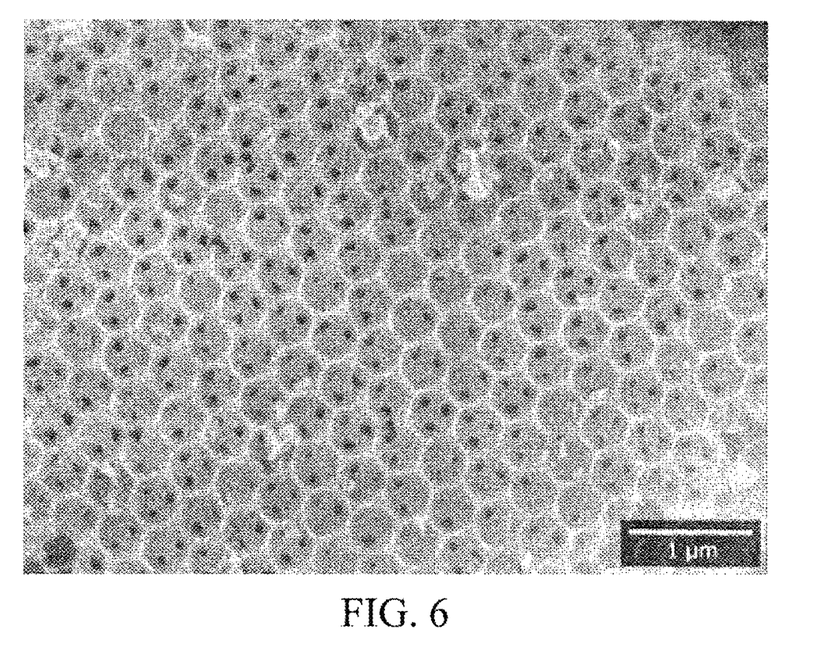
FIG. 6 represents a SEM image of the inverse opal as obtained in example 3.

A SEM image allows verifying the ordered structure of the material, with pores perfectly aligned and allows verifying the required pore diameter distribution, i.e. a homogeneous pore diameter.

FIG. 6 represents said SEM image.

Measurements

The corresponding reflectance measurements were carried out on a detector diode spectrophotometer Hewlett Packard 8452A for illustrating the color intensity variation depending on the calcination temperature of particles P3.

| | Calcination temperature | | |
|---|---|---|---|
| | 550° C. | 750° C. | 800° C. |
| Reflectance (%) | 12% $\lambda_{max}$ 640 nm | 11% $\lambda_{max}$ 650 nm | 19% $\lambda_{max}$ 680 nm |

Measurements

The corresponding reflectance measurements were carried out on an integrating sphere RT-060-SF LabSphere for illustrating the influence of the particle size on the reflectance for particles P1, P2 and P3 before and after sieving.

| Particles | Reflectance |
|---|---|
| Blue (P1) | |
| particles with size between 1 and 500 μm centered around 38 μm. | 9% |
| particles with size between 3 and 15 μm centered around 6 μm. | 11% |
| Green (P2) | |
| particles with size between 1 and 500 μm centered around 40 μm. | 13% |
| particles with size between 3 μm and 15 μm centered around 6 μm. | 14.5% |
| Red (P3) | |
| particles with size between 1 and .500 μm. centered around 40 μm. | 9% |
| particles with size between 3 and 15 μm centered around 9.5 μm. | 9.5% |

Example 4: Comparative Example with and without Hydrophobic Component Coating

Particles P1, P2, P3 and their ordered macroporous materials counterparts with no polyorganosiloxane coating were dispersed at 2% in weight in a water/propyleneglycol blend (70/30 w/w) and then deposited 200 μl of the dispersion onto a glass blade the deposit being dried 15 min at ambient temperature (25° C.). The diffuse reflectance was measured with an integrating sphere RT-060-SF LabSphere and the Half bandwidth is also measured to determine the chromaticity of the color, (a small bandwidth of around 50 nm is related to a high chroma value, and a large bandwidth of around 200 nm is related to a very low chroma value and a dull color).

| Particles | Reflectance | Half bandwidth |
|---|---|---|
| Blue particles without polyorganosiloxane coating | 2% | Larger than 200 nm |
| Blue particles P1 (with polyorganosiloxane coating) | 19% | 74 nm |
| Greenparticles without polyorganosiloxane coating | 1% | Larger than 200 nm |
| Green particles P2 (with polyorganosiloxane coating) | 17% | 85 nm |
| Red particles without polyorganosiloxane coating | 2% | Larger than 200 nm |
| Red particles P3 (with polyorganosiloxane coating) | 16% | 78 nm |

As illustrated by the measurement, a non-coated particle loss totally its vivid color and turn to brownish color. On the contrary, a coated particle with a polyorganosiloxane keeps its vivid color and its reflectance intensity.

Example 5: Cosmetic Compositions Comprising Inorganic Particles P1, P2 and/or P3

| Ingredients (% in weight) | E1 | E2 | E3 |
|---|---|---|---|
| MAGNESIUM SULFATE | 0.7 | 0.7 | 0.7 |
| PHENOXYETHANOL | 0.6 | 0.6 | 0.6 |
| CYCLOPENTASILOXANE (and) DISTEARDIMONIUM HECTORITE (and) PROPYLENE CARBONATE (BENTONE GEL VS-5 PC V HV from Elementis) | 5.80 | 5.82 | 5.82 |
| PARTICLE P1 | 2.5 | 2.5 | 2.5 |
| PARTICLE P2 | | 2.5 | 2.5 |
| PARTICLE P3 | | | 2.5 |
| ISODODECANE | 1.80 | 1.8 | 1.8 |
| WATER | 83.6 | 81.1 | 78.6 |
| POLYGLYCERYL-4 ISOSTEARATE (and) CETYL PEG/PPG-10/1 DIMETHICONE (and) HEXYL LAURATE (Abil WE 09 from Evonik Goldschmidt) | 5.0 | 5.0 | 5.0 |

5.1. A composition E1 was prepared comprising 2.5% by weight of particles P1 with respect to the total weight of the dispersion.

5.2. A composition E2 was prepared comprising 2.5% by weight of particles P1 and 2.5% by weight of the particles P2 with respect to the total weight of the dispersion.

5.3. A composition E3 was prepared comprising 2.5% by weight of particles P1, 2.5% by weight of particles P2 and 2.5% by weight of the particles P3 with respect to the total weight of the dispersion.

Said compositions E1, E2, E3 were applied to the skin, the thickness of the deposit formed onto the skin being around 50 μm. After application on the skin:
Composition E1 gives an intensive luminous Blue reflection,
Composition E2 gives a bluish green color reflection, and
Composition E3 gives an enlightenment of the skin color.

Example 6: Application Tests

Dispersion as described in example 5 is applied on a "skin like" support (disc of elastomer having smooth surface and a color some similar to the skin color) so as to form a film 50 μm thick, which is dried 15 min at ambient temperature.

6.1 dispersions E1, E2, E3 of example 5 were applied on a "skin like support" as a thin film of 50 μm.

Each experiment is performed with a comparative zone of the "skin like" support non treated so as to observe the difference in the aspect.

The color of the deposit formed on the skin have been measured with a Konica Minolta CM2600D spectrocolorimeter and the "Hunter values" (L, a, b) are reported in the following table:

6.2. Results

| Composition applied | Observation | ΔL | Δa | Δb |
|---|---|---|---|---|
| Application of composition E1 | The appearance of the substrate is transparent light blue in comparison with a substrate without application of composition 5.1.1 | −29 | −46 | −57 |

-continued

| Composition applied | Observation | ΔL | Δa | Δb |
|---|---|---|---|---|
| Application of composition E2 | The appearance of the substrate is transparent and the hue is enlightened in comparison to a substrate without application of composition 5.1.2 | 5 | −3 | −15 |
| Application of composition E3 | The appearance of the substrate is transparent and the hue is significantly enlightened in comparison to a substrate without application of composition 5.1.3 | 10 | 1 | −2 |

The present example clearly shows that dulling and opaque appearances of the skin substrate are avoided. Transparence is observed for each application.

Moreover, it further illustrates that mixtures of reflecting ordered macroporous materials according to the present invention may be carried out for obtaining an enlightenment of the skin color.

The invention claimed is:

1. An inorganic material comprising particles of three-dimensional ordered macroporous structure comprising spherical pores,
    said pores having an average pore diameter ranging from 50 nm to 10 μm,
    the pore diameter varying by no greater than 20%,
    the surface of said pores being coated by an absorber agent of the visible wavelength spectrum,
    said particles having an average largest dimension ranging from 1 to 40 μm, and wherein
    said particles are coated through an infiltration step followed by a heating step with at least a hydrophobic component selected from the group consisting of polydimethylsiloxanes (PDMS), phenyltrimethicones, phenyldimethicones, trimethylsiloxyphenyl dimethicones, phenyl trimethylsiloxy diphenylsiloxanes, diphenyl dimethicones, diphenyl methyldiphenyl trisiloxanes, and mixtures thereof, and
    said hydrophobic component coating the inorganic material on its external surface and its internal surfaces of the pores within the particles.

2. An inorganic material according to claim 1, wherein the inorganic material is a metallic oxide of metal having a valency between 1 and 6, the metal being selected from the group consisting of titanium, iron, copper, magnesium, calcium, barium, aluminium, zinc, zirconium, strontium, silicon, tin, bismuth, and cerium.

3. An inorganic material according to claim 1, wherein the inorganic material is a metallic oxide selected from the group consisting of $TiO_2$, $Al_2O_3$, ZnO, MgO, CaO, and $Si_xO_y$, with x and y comprised independently from another between 0.1 and 2.

4. An inorganic material according to claim 1, wherein the inorganic material is a metallic oxide selected from the group consisting of $SiO_2$, $TiO_2$, and $Al_2O_3$.

5. An inorganic material according to claim 1, wherein the average pore diameter ranges between 50 nm and 1 μm.

6. An inorganic material according to claim 1, wherein the average pore diameter ranges between 0.2 and 0.6 μm.

7. An inorganic material according to claim 1, wherein the pore diameter varies by no greater than 5%.

8. An inorganic material according to claim 1, wherein the absorber agent is selected from the group consisting of polyphenols, melanines, eumelanines, aromatic azomethines, heteroaromatic azomethines, carbon black, and black metallic oxides.

9. An inorganic material according to claim 1, wherein the absorber agent is present in an amount ranging from 1% to 20% by weight relative to the total weight of the particles without any coating with a hydrophobic component.

10. An inorganic material according to claim 1, wherein the absorber agent is present in an amount ranging from 3 to 10% by weight relative to the total weight of the particles without any coating with a hydrophobic component.

11. An inorganic material according to claim 1, wherein the average largest dimension of the particles ranges from 5 to 10 μm.

12. An inorganic material according to claim 1, wherein the hydrophobic component is a polydimethylsiloxane.

13. A process for manufacturing an inorganic material comprising particles of three-dimension ordered macroporous structure comprising spherical pores;
    said pores having an average pore diameter ranging from 50 nm to 10 μm,
    the pore diameter varying by no greater than 20%,
    the surface of said pores being coated by an absorber agent of the visible wavelength spectrum, and
    said particles having an average largest dimension ranging from 1 to 40 μm, the process comprising the steps of:
    (i) providing a colloidal crystal formed of a regular array of monodisperse organic polymer particles as a template,
    (ii) adding a precursor thereof, so as to produce a solid into the interstices between the monodisperse particles of the colloidal crystal and to form a solid continuous phase and a composite colloidal crystal thereof, wherein the material can optionally comprise at least one absorber agent of the visible wavelength spectrum and/or at least one precursor of an absorber agent of the visible wavelength spectrum,
    (iii) removing the monodisperse particles so as to form a regular array of pores in the solid continuous phase, and
    (iv) applying a coating through an infiltration step followed by a heating step onto the surface of the particles, said coating comprising at least one hydrophobic component selected from the group consisting of polydimethylsiloxanes (PDMS), phenyltrimethicones, phenyldimethicones, trimethylsiloxyphenyl dimethicones, phenyl trimethylsiloxy diphenylsiloxanes, diphenyl dimethicones, diphenyl methyldiphenyl trisiloxanes, and mixtures thereof,
    said hydrophobic component coating the inorganic material on its external surface and its internal surfaces of the pores within the particles.

14. The process according to claim 13, wherein step (iv) consists in dispersing the particles as obtained in step (iii) in a solution containing a hydrophobic component, spinning the obtained impregnated particles and carrying out a heating step at a temperature ranging from 100 to 800° C.

15. An inorganic material according to claim 1, wherein the heating step is conducted at a temperature of 300° C. to 600° C.

16. An inorganic material according to claim 1, wherein the hydrophobic component is fixed on said particles through said heating step.

17. An inorganic material according to claim 1, wherein the inorganic material is a metallic oxide selected from the group consisting of $TiO_2$, $Fe_2O_3$, $Al_2O_3$, CuO, ZnO, $ZrO_2$, MgO, CaO, BaO, $SiO_2$, $SnO_2$, $Bi_2O_3$, $CeO_2$, $SrO_2$, $BaTiO_3$, $Bi_4Ti_3O_{12}$, $Bi_{12}SiO_{20}$, and $Si_xO_y$, with x and y comprised independently from another between 0.1 and 2.

* * * * *